(12) United States Patent
Douglas et al.

(10) Patent No.: US 11,253,419 B2
(45) Date of Patent: Feb. 22, 2022

(54) WEARABLE ACTIVE-COMPRESSION THERAPY AND TREATMENT

(71) Applicant: Nextern, Inc., White Bear Lake, MN (US)

(72) Inventors: Ryan Douglas, Stillwater, MN (US); Casey Carlson, Independence, MN (US)

(73) Assignee: NEXTERN, INC., White Bear Lake, MN (US)

( * ) Notice: Subject to any disclaimer, the term of this patent is extended or adjusted under 35 U.S.C. 154(b) by 285 days.

(21) Appl. No.: 16/654,459

(22) Filed: Oct. 16, 2019

(65) Prior Publication Data
US 2020/0060926 A1    Feb. 27, 2020

Related U.S. Application Data

(63) Continuation of application No. 14/965,668, filed on Dec. 10, 2015, now Pat. No. 10,492,978.

(60) Provisional application No. 62/090,088, filed on Dec. 10, 2014.

(51) Int. Cl.
*A61H 9/00* (2006.01)
*A61F 5/01* (2006.01)

(52) U.S. Cl.
CPC .......... *A61H 9/0078* (2013.01); *A61F 5/012* (2013.01); *A61H 9/0092* (2013.01); *A61H 2201/0207* (2013.01); *A61H 2201/0214* (2013.01); *A61H 2201/0242* (2013.01); *A61H 2201/165* (2013.01); *A61H 2201/5012* (2013.01);

(Continued)

(58) Field of Classification Search
CPC ............ A61H 9/00–0007; A61H 9/005; A61H 9/0078–0092; A61H 2201/0103; A61H 2201/165; A61H 2201/5012; A61H 2201/5056; A61H 5501/5071; A61H 2201/5097; A61H 2209/00; A61F 5/012
See application file for complete search history.

(56) References Cited

U.S. PATENT DOCUMENTS

| | | | |
|---|---|---|---|
| 2005/0107725 A1* | 5/2005 | Wild | A61H 9/0078 601/152 |
| 2007/0055188 A1* | 3/2007 | Avni | A61F 13/041 601/151 |

(Continued)

*Primary Examiner* — Rachel T Sippel
(74) *Attorney, Agent, or Firm* — Craige Thompson; Thompson Patent Law; Timothy D. Snowden (57) ABSTRACT

Apparatus and associated methods relate to a wearable compression therapy system for ambulatory therapy, the system including a wearable garment having one or more inflatable chambers, and a pneumatic engine locally coupled to the garment to provide control and inflation of the one or more inflatable chambers. In an illustrative embodiment, the pneumatic engine may control a pump and one or more valves to inflate the inflatable chambers. The valves and pump may be coordinated according to a pre-programmed profile. In some embodiments, the pneumatic engine may have a wireless interface configured to receive control signals from a remote mobile device untethered from the garment. The pneumatic engine may send to the remote mobile device signals indicative of sensed conditions of the compression therapy system. In some embodiments, the pneumatic engine may include a power source that advantageously permits the user to be untethered from a source of power.

20 Claims, 5 Drawing Sheets

(52) U.S. Cl.
CPC ........... *A61H 2201/5043* (2013.01); *A61H 2201/5071* (2013.01); *A61H 2201/5097* (2013.01); *A61H 2205/02* (2013.01); *A61H 2205/04* (2013.01); *A61H 2205/06* (2013.01); *A61H 2205/08* (2013.01); *A61H 2205/10* (2013.01); *A61H 2205/12* (2013.01); *A61H 2230/045* (2013.01); *A61H 2230/505* (2013.01)

(56) References Cited

U.S. PATENT DOCUMENTS

| | | | | |
|---|---|---|---|---|
| 2007/0249977 | A1* | 10/2007 | Bonnefin | A61H 9/0078 602/13 |
| 2008/0262399 | A1* | 10/2008 | Kovelman | A61H 9/0078 601/152 |
| 2010/0324429 | A1* | 12/2010 | Leschinsky | A61B 17/135 600/493 |
| 2011/0230806 | A1* | 9/2011 | Lou | A61F 5/012 602/13 |
| 2012/0265240 | A1* | 10/2012 | Ganske | A61H 9/0078 606/202 |
| 2014/0303533 | A1* | 10/2014 | Zeutzius | A61H 9/0092 601/151 |
| 2015/0150746 | A1* | 6/2015 | Yurko | A61H 9/0078 601/150 |
| 2015/0313608 | A1* | 11/2015 | Baudenbacher | A61B 17/1355 601/150 |
| 2016/0000640 | A1* | 1/2016 | Lai | A61H 9/0092 601/149 |
| 2017/0196763 | A1* | 7/2017 | Obma | A61H 9/0092 |

\* cited by examiner

WEARABLE ACTIVE-COMPRESSION THERAPY AND TREATMENT

CROSS-REFERENCE TO RELATED APPLICATIONS

This application is a continuation of U.S. patent application Ser. No. 14/965,668, entitled "Wearable Active-Compression Therapy And Treatment System", filed by Ryan Douglas on Dec. 10, 2015, which claims the benefit of U.S. Provisional Application Ser. No. 62/090,088, entitled "Wearable Active-Compression Therapy and Treatment System," filed by Douglas, on Dec. 10, 2014. This application incorporates herein the entirety of the foregoing documents by reference.

TECHNICAL FIELD

Various embodiments relate generally to wearable pneumatic compression therapy devices.

BACKGROUND

Compression therapy and/or massage therapy is used in treating various diseases and injuries. Compression therapy is a non-invasive mechanical method used for a variety of therapies and treatments. Compression therapy may be used to aid in the healing of wounds. Injuries that require portions of the body to be stabilized during recovery may use compression therapy to aid in such stabilization. Compression therapy may be used in the treatment of venous leg ulcers. Various forms of compression therapy may be used to treat Edema. Deep vein thrombosis may involve compression therapy in a treatment regime.

Compression therapy may be performed using active methods and/or passive methods. Passive methods may include the use of compression bandages and compression garments. Compression garments may be garments that have an elastic that provides compression to a location on the body. Tight-fitting leggings may be worn to provide compression of the legs, for example. Tight-fitting sleeves may be worn to provide compression of an arm, for example. Active methods may include the use of pneumatic pumps and inflatable chambers configured to provide pressure to parts of the human body.

SUMMARY

Apparatus and associated methods relate to a wearable compression therapy system for ambulatory therapy, the system including a wearable garment having one or more inflatable chambers, and a pneumatic engine locally coupled to the garment to provide control and inflation of the one or more inflatable chambers. In an illustrative embodiment, the pneumatic engine may control a pump and one or more valves to inflate the inflatable chambers. The valves and pump may be coordinated according to a pre-programmed profile. In some embodiments, the pneumatic engine may have a wireless interface configured to receive control signals from a remote mobile device untethered from the garment. The pneumatic engine may send to the remote mobile device signals indicative of sensed conditions of the compression therapy system. In some embodiments, the pneumatic engine may include a power source that advantageously permits the user to be untethered from a source of power.

Various embodiments may achieve one or more advantages. For example, the local coupling of the pneumatic engine to the wearable garment may reduce or eliminate tubing. Reduced or eliminated tubing may prevent accidents due to the tubing being caught on an object. Providing control via a remote mobile device may reduce the form factor of the garment and pneumatic engine. A reduced form factor may promote user mobility and/or flexibility during compression therapy. For example, a user may work at a desk while simultaneously undergoing compression therapy of an arm or a leg. In some embodiments, the controller may be integrated into the wearable garment such that the device can provide therapy while untethered to a physical location, and/or while operating autonomously without connection to any external peripheral devices (e.g., no mobile devices needed for control). In some embodiments, the user may be ambulatory such that the user is able to walk about while undergoing compression therapy, which may dramatically reduce recovery times and improve patient outcomes, for example, relative to therapy while mechanically tethered to another device.

The remote mobile device may include sophisticated programming options. For example, a therapy schedule may adapt to ambient temperature and/or barometric pressure, for example. In some embodiments, a therapy schedule may be adapted in response to a calculated health metric. In an exemplary embodiment, a therapy schedule may be reduced in response to an improving calculated health metric. Such adaptive therapy schedules may minimize inconvenience to a user who is undergoing therapy. Minimizing the therapy time may promote positive mental health.

In some embodiments, the inflatable chambers may be incorporated in a shirt or pants, for example. The user may don the shirt or pants having the inflatable chambers as otherwise normal clothing. And when it is time for the user's daily therapy, a system controller may automatically provide airflow to the inflatable chambers, for example. Such automatic control may help a user to comply with a doctor's prescribed therapy regime. Regular compliance of a therapy regime may improve the positive health benefits of such a therapy regime.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, an exemplary untethered active compression therapy device is briefly introduced with reference to FIG. 1. Second, with reference to FIG. 2, exemplary system components of a wearable compression therapy system are detailed. Then, with reference to FIG. 3, an exemplary method of automatically performing a compression therapy schedule will be described. Finally, with reference to FIG. 4, an exemplary method of using measured therapy metrics to adjust a therapy schedule will be described.

Figure 1:
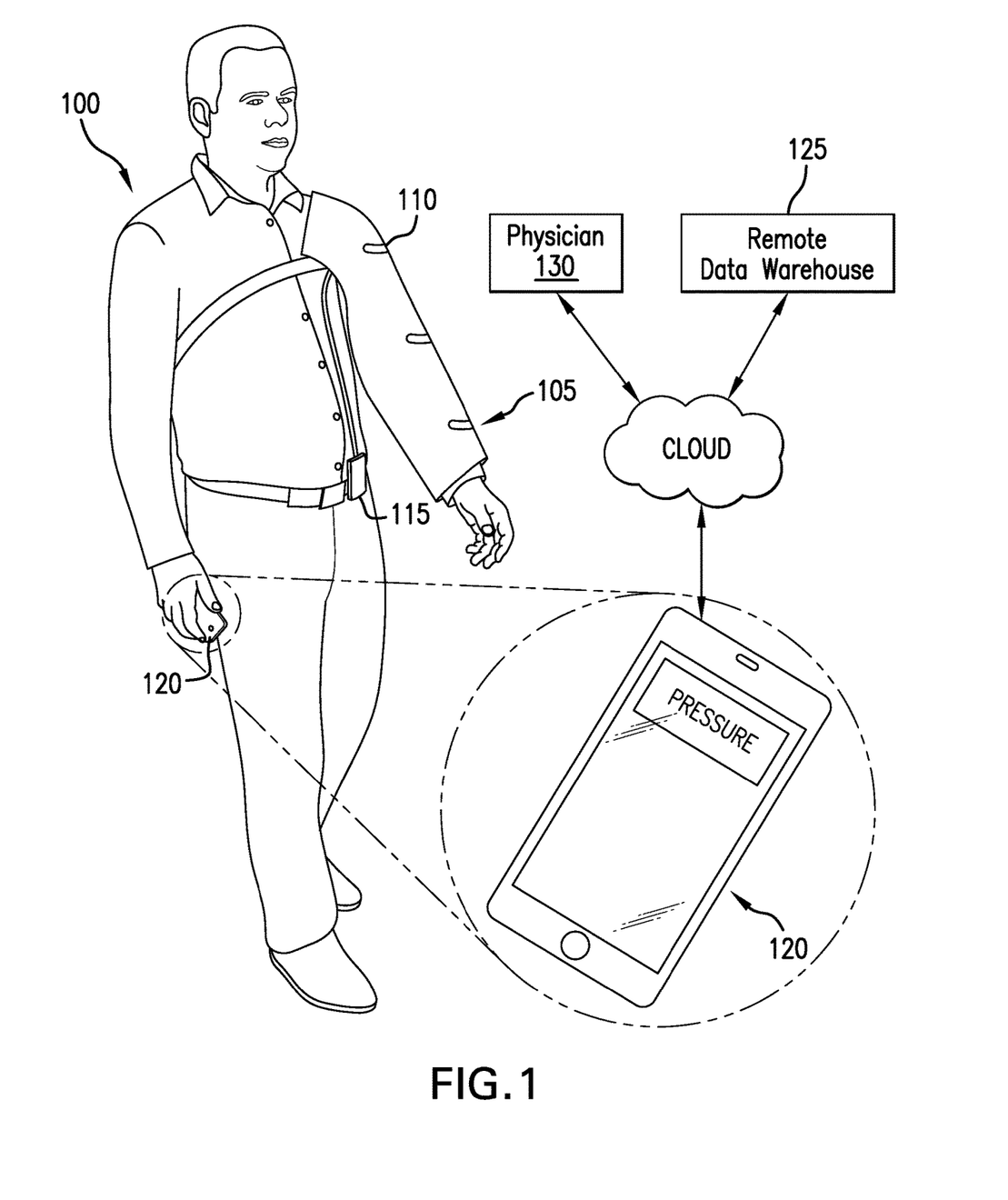
FIG. 1 depicts a scenario in which a user is wearing an exemplary active compression therapy system.

FIG. 1 depicts a scenario in which a user is wearing an exemplary active compression therapy system. In the FIG. 1 depiction, a user 100 of an untethered compression therapy system 105 is walking about. The compression therapy system 105 includes an inflatable garment 110, a wearable controller 115, and a mobile device 120 running a pneumatic therapy application ("APP"). The mobile device 120 and the wearable controller 115 may be in wireless communication with one another, for example. The wearable controller 115, may include a pneumatic pump for generating air pressure. The wearable controller 115 may include one or more valves to control airflow to and/or from the inflatable garment 110. One or more sensors may be included in inflatable garment 110 and/or the wearable controller 115 to monitor one or more parameters of the untethered compression therapy system 105. For example, a pressure sensor in the wearable controller 115 may be indicative of the pressure applied to the user's arm by the inflatable garment 110. The wearable controller 115 may compare a signal of the pressure sensor to a predetermined threshold. The wearable controller 115 may control the pneumatic pump and/or the valves in response to the comparison, for example. The wearable controller 115 may advantageously maintain a pressure in the inflatable garment 110 that is substantially equal to a therapy pressure that is predetermined by a therapy routine, while permitting the user 100 to remain mobile and untethered to a control device or a power source.

The APP running on the mobile device 120 may be configured to communicate with a remote data warehouse 125. The APP may log data associated with a therapy session being conducted on the user 100, for example. The APP may send the logged data to the remote data warehouse 125 where other users' data may be also received. The remote data warehouse 125 may communicate the user's data to a physician 130 under whom the user 100 is being treated. The physician 130 may alter the therapy schedule of the user 100 in response to the communicated user's data, for example. The altered therapy schedule may then be sent to the mobile device 120, for example. The next day's therapy session may begin, for example, with the mobile device sending signals corresponding to the revised therapy session to the wearable controller 115 so the wearable controller may send signals to the pneumatic pump and air valves that may comply with the revised therapy session.

For example, if the user's data is indicative of the user 100 not improving as much and/or as quickly as the physician expected, the physician 130 may intensify the therapy regime associated with the user 100. Conversely, if the user's data is indicative of the user 100 showing significant improvement, the physician 130 may reduce the intensity of the therapy regime associated with the user 100. In some embodiments, the remote data warehouse 125 may provide data analysis on the data from many users. These data may be used to determine therapy system parameters that are likely to provide successful therapy, and/or therapy system parameters that are unlikely to provide successful therapy.

A user's data may be analyzed to evaluate the therapy system 105 itself. For example, if the therapy system 105 has a pneumatic pump that is degrading, the data warehouse may discover this condition when comparing the user's current data with the user's past data. The data warehouse may notify the user that the therapy system 105 needs maintenance or replacement, for example.

Figure 2:
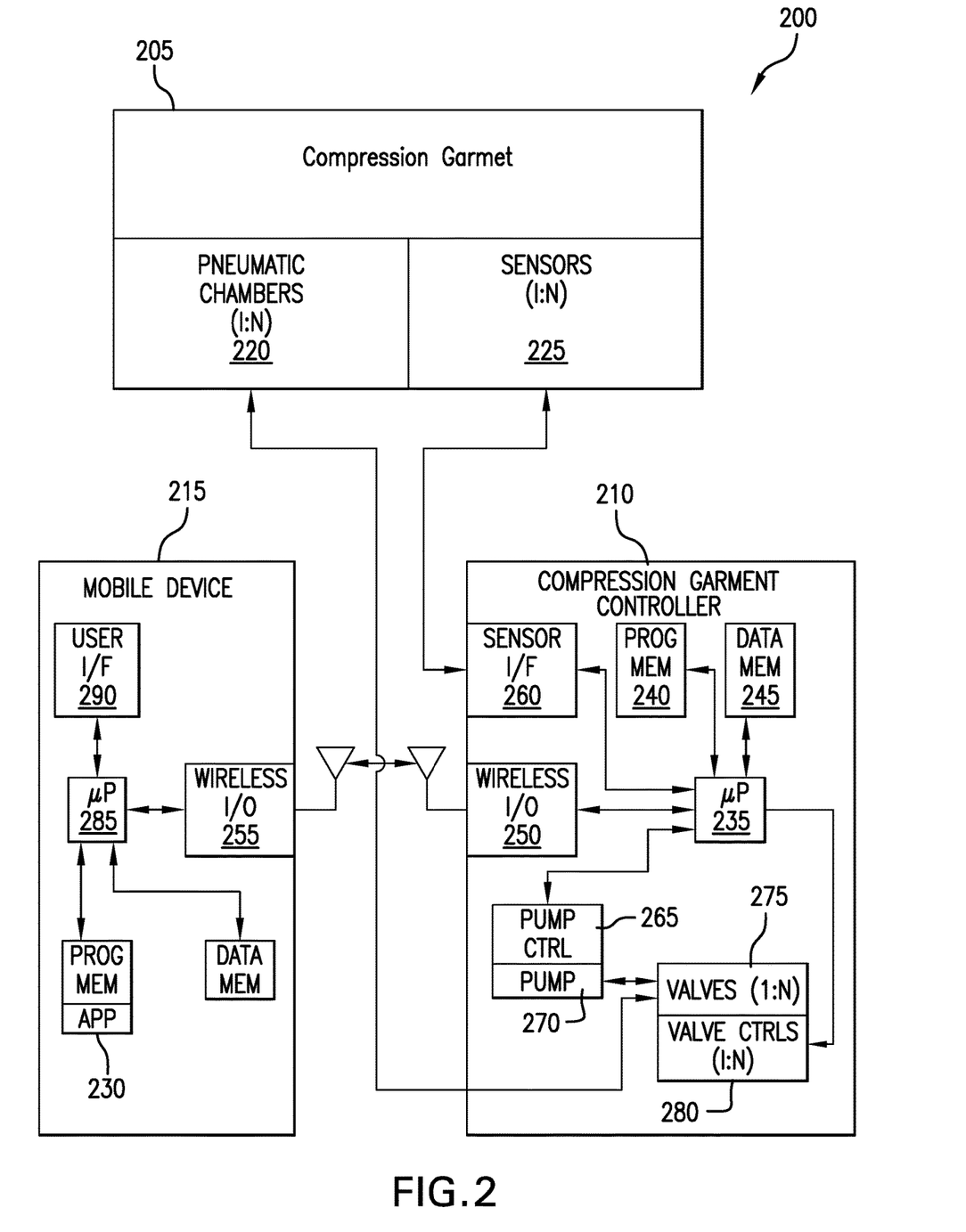
FIG. 2 depicts a block diagram of an exemplary untethered wearable active compression therapy system.

FIG. 2 depicts a block diagram of an exemplary untethered wearable active compression therapy system. In FIG. 2, a block diagram 200 of an exemplary untethered wearable active compression therapy system includes a compression garment 205, a compression garment controller 210 and a mobile device 215. The compression garment 205 includes a plurality of N pneumatic chambers 220. The compression garment 205 also includes a pressure sensor 225 for each of the N pneumatic chambers 220. In some embodiments the compression garment controller may include a pressure sensor for one or more of the pneumatic chambers 220, for example.

The compression garment controller 210 is configured to provide airflow to and from the N pneumatic chambers 220 of the compression garment 205. The compression garment controller 210 is configured to receive signals from the N pressure sensors 225 of the compression garment 205. The compression garment controller is configured to wirelessly communicate with the mobile device 215, upon which an APP 230 is running. In some embodiments, the compression garment controller 210 may be configured to perform a compression therapy session independently of the mobile device 215. In some embodiments, the compression garment controller 210 may be configured in such a way as to require regular communications with the mobile device 215 during a compression therapy session.

The depicted compression garment controller 210 has a microprocessor 235 which executes a program stored in program memory 240. The microprocessor 235 may use data memory 240 for storing data being used during a compression therapy session, for example. The microprocessor 235 may be in electrical communication with a wireless input/output module 250. In some embodiments a wireless communications link may be established between a wireless input/output module 255 of the mobile device 215 and the wireless input/output module 250 of the compression garment controller 210. For example, the mobile device 215 and the compression garment controller may be paired and use a Bluetooth wireless communications standard. In some embodiments, various communications protocols may be used. For example, Wi-Fi or near field communications protocols may be used. In an exemplary embodiment, cellphone communications standards may be used.

The depicted compression garment controller 210 includes a sensor interface module 260, which is configured to receive signals from the pressure sensors 225 of the compression garment 205. The compression garment controller 210 includes a pump controller 265 and a pneumatic pump 270. The compression garment controller 210 includes one or more valves 275 which receive air from the pump 270 and supply air to the one or more pneumatic chambers 220 of the compression garment 205. In some embodiments, the valves 275 may be located in the compression garment 205. The valves 275 may be controlled by the microprocessor 235 via one or more valve controllers 280. The valve controllers 280 may be located in the compression garment 205, in some embodiments.

The mobile device has a microprocessor 285 that executes the instructions associated with the APP 230. The APP 230 may have instructions that correspond to a Graphical User Interface ("GUI"). The microprocessor 285 may send and/or receive signals to/from a user interface 290 that correspond to the GUI. For example, the APP 230 may have instructions that sound an alarm when it is time for a therapy routine to be executed. The processor 285 may send signals that present a graphical button on a display screen. When the button is pressed by the user, a signal is generated and received by the microprocessor 285, the signal indicative of the user's initiation of the scheduled therapy routine. The microprocessor 285 may send one or more signals corresponding to such an event to the compression garment controller in response to receiving the begin therapy signal. The signals sent by the microprocessor 285 may include a predetermined pressure for one or more pneumatic chambers for example.

In some implementations, the compression garment controller may be attached to the garment and provides a wired or wireless communication interface for receiving command instructions, and executing those command instructions by operatively controlling one or more pumps or valves that are embedded in the compression garment 205. In addition, some embodiments may further provide for the status information about the garment controller 210 and its controlled devices (e.g., pump 270, valves (1:N) 275) to be communicated via the same interface. Such status information may also include information about an energy storage element (e.g., battery pack) integrated with the garment for supplying power to operate the garment 205 during therapy and/or while communicating with, for example, the mobile device 215. In some implementations, the interface for receiving command instructions and communicating status information may include an electrical connector for making galvanic connection between an external control device and the compression garment controller 210. If wired, the communication interface may also receive electrical power (e.g., 5, 12 or 24 DC), which may be processed by the garment for operating power and/or to recharge the energy storage element.

In some embodiments, the communication interface may also communicate measurement data collected by sampling using any of the sensors that may be operatively coupled to the compression garment controller 210. Some of the sensors that are operatively coupled to, and monitored by, the compression garment controller 210 may include optionally included sensors, such as temperature, SpO2, and/or pulse measurement sensors that can be, for example, releasably plugged into one or more external ports of the compression garment controller 210. Such external ports may advantageously provide customizable expansion of the array of sensors that are monitored by the compression garment controller 210.

In some embodiments, the compression garment controller 210 may be configured as a packaged module that releasably couples to the compression garment 205. In such embodiments, some elements of the compression garment controller 210 may be housed in the packaged module, and then operatively coupled to operate the compression garment upon being plugged into an electrical connector. In an example, the packaged module may be received in a pocket formed on the garment, for example. The packaged module may make operative connection to the electrical connector when the module is inserted fully into the pocket so that the packaged module seats on the electrical connector. Upon connection to the electrical connector attached to the garment, the controller module may provide functional control for operating the compression garment 205 to deliver a predetermined treatment profile to the patient. The compression garment controller 210 may operate in a stand-alone capacity to deliver compression therapy according to a predetermined profile stored in a memory, such as the memory devices 240, 245.

Some embodiments may further operatively communicate with an external command device, such as the mobile device 215, which may provide additional functionality. For example, the external command device may communicate with one or more remote servers to obtain updates for the operating system, application program(s), and/or configuration parameters usable by the compression garment controller 210 to operate the untethered wearable active compression therapy system 200.

Examples of additional functionality may include updating therapy algorithms such as, for example, sequenced inflation and deflation of selected pneumatic chambers to provide a "kneading" effect that promotes the movement of lymph toward or away from a desired region of the body. In an illustrative example, each inflation cycle may begin with inflation of the central-most chambers, followed by successive inflation of chambers at increasing distance from the center of the garment, which may promote the flow of lymph away from the portion of the limb in contact with the center of the compression garment 205. In such a fashion, lymph may be directed to or away from a selected location by progressive inflation and deflation of selected ones of the pneumatic chambers (1:N) 220.

Figure 3:
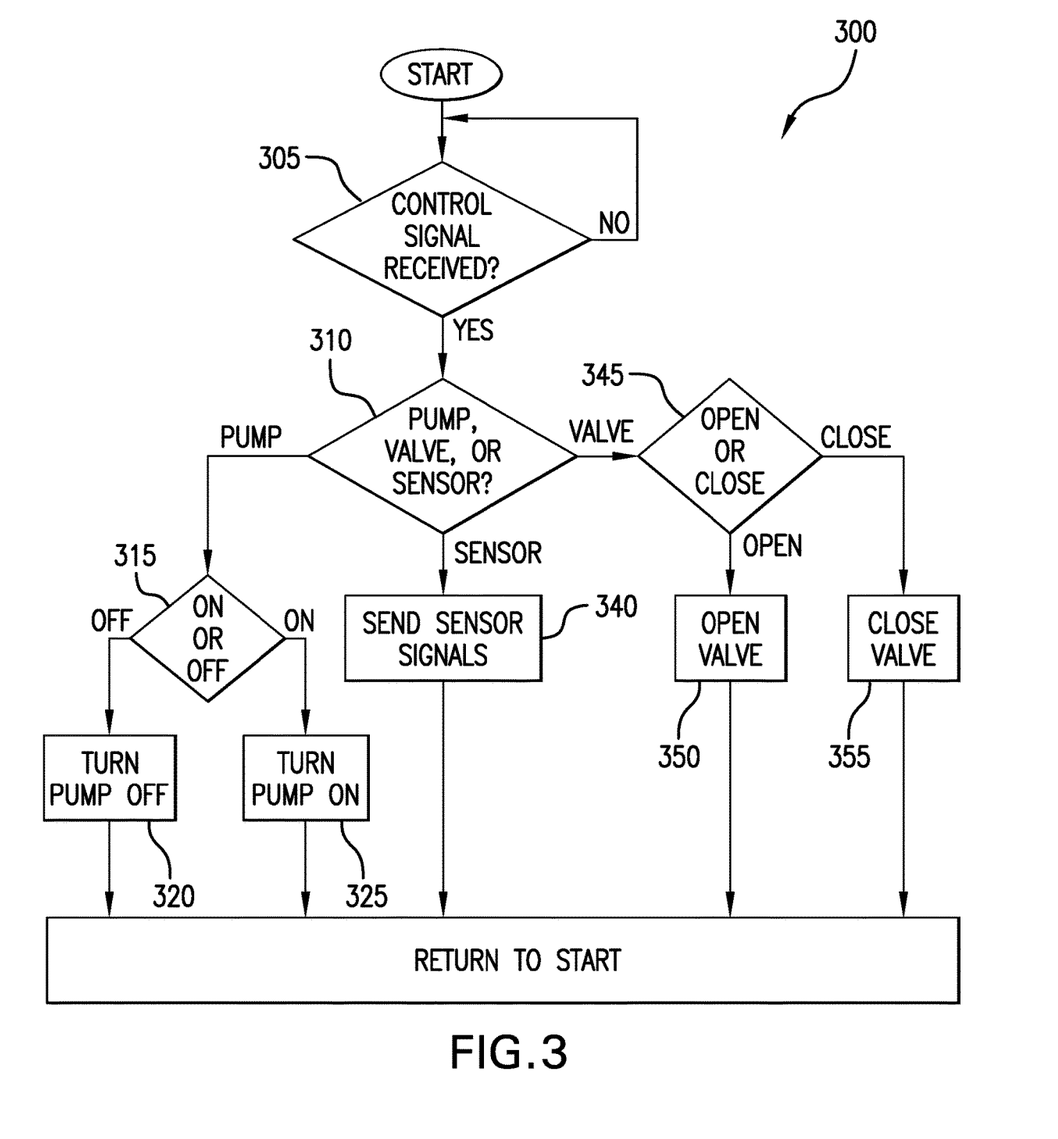
FIG. 3 depicts a flowchart of an exemplary control method of an exemplary compression therapy routine.

FIG. 3 depicts a flowchart of an exemplary control method of an exemplary compression therapy routine. In FIG. 3, an exemplary method of compression therapy 300 is shown. In some embodiments, such as the exemplary one depicted in FIG. 3, a compression garment controller 210 may be configured to operate under the direction of a remote mobile device 215. The exemplary method 300 is given from the perspective of the microprocessor 235 of the compression therapy controller 210. The method 300 begins with the microprocessor 235 waiting 305 to receive a control signal from the wireless interface module 250. If the microprocessor 235 doesn't receive a control signal from the wireless interface module 250, the microprocessor 235 continues to wait at step 305. If, however, the microprocessor receives a control signal, then the microprocessor evaluates 310 the control signal as to whether it is related to control of the pneumatic pump 270, the valves 275, or the sensors 225. If the control signal is related to the pneumatic pump 270, the microprocessor 235 evaluates 315 the control signal as to whether it is an instruction to turn on the pump 270 or to turn off the pump 270. If the control signal is evaluated to be a turn-pump-on signal, the microprocessor 235 sends 320 an on-signal to the pump controller 265. If, however, the control signal is evaluated to be a turn-pump-off signal, the microprocessor 235 sends 325 an off-signal to the pump controller 265. After sending either an on-signal or an off-signal to the pump controller 265, the method returns to step 305 and the microprocessor 235 awaits the next control signal.

If, at step 310, the received control signal is evaluated to be a sensor signal, the microprocessor 235 receives the signals generated by the sensors 225 and sends 340 the received sensor signals to the wireless input/output module 250. After sending the received sensor signals to the wireless input/output module 250, the method 300 returns to step 305 and the microprocessor 235 awaits the next control signal.

If, at step 310, the received control signal is a valve signal, the microprocessor 235 evaluates 345 whether it is an open-valve command or a close-valve command. If the control signal is evaluated to be a valve-open command, the microprocessor 235 sends 350 an open-command signal to a valve controller 280 associated with the command signal. If, however, the control signal is evaluated to be a valve-close command, the microprocessor 235 sends 355 a close-command signal to a valve controller 280 associated with the command signal. After sending either an open signal or a close signal to a valve controller 280 associated with the command signal, the method 300 returns to step 305 and the microprocessor 235 awaits the next control signal.

Figure 4:
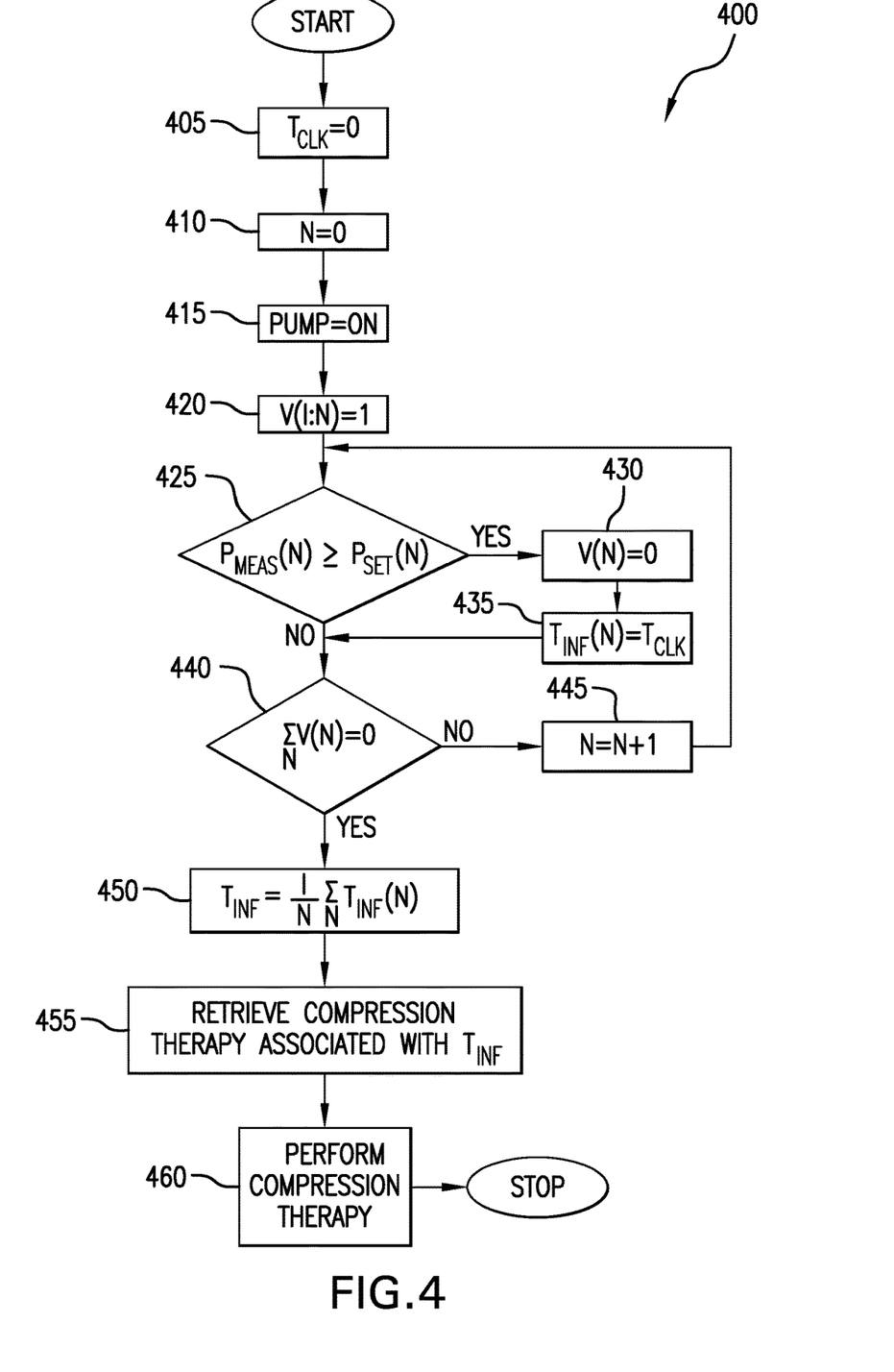
FIG. 4 depicts a flowchart of an exemplary method of adaptively selecting a therapy session associated with a patient's tissue condition.

FIG. 4 depicts a flowchart of an exemplary method of adaptively selecting a therapy session associated with a patient's tissue condition. In FIG. 4, an exemplary method of adaptively selecting a therapy session 400 is shown. In some embodiments, such as the exemplary one depicted in FIG. 4, a compression garment controller 210 may be configured to operate independently of a remote mobile device 215. The exemplary method 400 is given from the perspective of the microprocessor 235 of the compression therapy controller 210. The method 400 begins with the microprocessor 235 initializing the clock, Tclk, to zero, 405. The microprocessor 235 then initializes the chamber index, N, to zero, 410. Then the microprocessor sends 415 an on signal to the pump controller 265 to turn on the pneumatic pump 270. The microprocessor 235 then sends 420 the N valve controllers 280 an open signal (indicated by V(N)=1). Some embodiments may adaptively select a therapy session or adaptively adjust a treatment protocol as a function of a patient's disease state. In some implementations, a patient's disease state may comprise the patient's tissue condition. Various implementations may adaptively select a therapy session or adjust a treatment protocol as a function of a patient's disease state, using artificial-intelligence techniques for adaptive treatment adjustment such as those disclosed with reference to FIGS. 2 and 3 of U.S. application Ser. No. 14/936,462, titled "Dynamically Controlled Treatment Protocols in Close Loop Autonomous Treatment Systems", filed by Ryan Douglas, on 9 Nov. 2015, the entire contents of which are herein incorporated by reference.

The microprocessor 235 then receives a signal, Pmeas(N), from the pressure sensor associated with the current index, N, and compares 425 the received signal, Pmeas(N), with a predetermined threshold, Pset(N). If the received signal, Pmeas(N) is greater than the predetermined threshold, Pset(N), then the microprocessor sends 430 an off signal to the valve controller 280 associated with the current index, N. The processor 235 then assigns 435 the inflation time, Tinf(N), associated with the current index, N, to be that of the elapsed clock time, Tclk. Then, or if at step 425, the received signal, Pmeas(N) is not greater than the predetermined threshold, Pset(N), then the microprocessor 235 evaluates 440 if all the valves are closed. If at least one of the valves is still open, the current index, N, is incremented 445 by one (or if N is at Nmax, then N is again initialized to zero. The microprocessor 235 then returns to step 425 and receives a signal, Pmeas(N), from the pressure sensor associated with the current index, N, and compares the received signal, Pmeas(N), with a predetermined threshold, Pset(N).

If, however, at step 440, all of the microprocessor 235 has evaluated that all of the valves are closed, the microprocessor 235 determines 450 the average inflation time of the chambers. Then the microprocessor 235 retrieves 455 a compression therapy schedule associated with the determined average inflation time. The high value of the average inflation time may correspond to a limb that has a relatively small volume, for example. A low value of the average inflation time may correspond to a limb that has a relatively large volume, for example. The relative small volume limb may indicate that only a small amount of fluid retention remains in the limb, for example. A less intensive therapy schedule may correspond to a small volume limb, whereas a more intensive therapy schedule may correspond to a large volume limb. The microprocessor 235 may then execute 460 the retrieved therapy schedule.

In some embodiments the controller may be configured to operate independent of a mobile device. For example, in various designs the controller may be pre-programmed with a range of appropriate therapies for a patient, according to a patient's personalized treatment profile. In some designs, a patient's personalized treatment profile may be determined as a function of one or more of: the patient's disease state, standards of care, a physician's prescription, intervention by a caregiver, or global population data. In some implementations, the controller may be configured to apply treatment and measure outcome, without a mobile device. In further embodiments, the controller may archive treatment compliance data for later upload to a central server or database. In some embodiments, a user control on an exemplary wearable device may permit a user to operate the controller directly, with or without a mobile device or connection to a central server or database. In various designs, the wearable device may download a therapy recipe to the controller, which then runs the recipe without connection to the mobile device.

Figure 5:
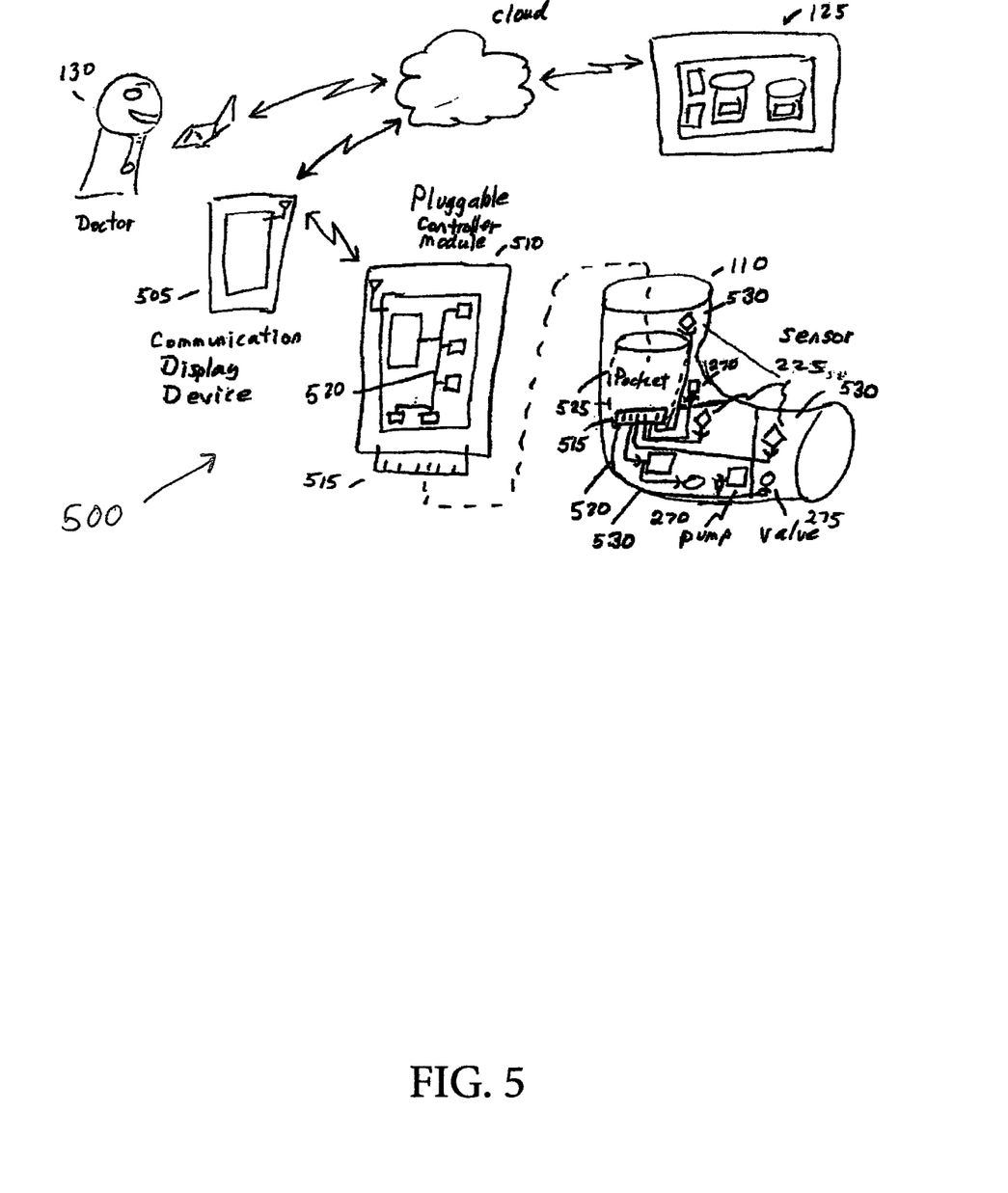
FIG. 5 depicts a schematic view of an exemplary detachable controller system for a wearable inflatable compression therapy garment.

FIG. 5 depicts a schematic view of an exemplary detachable controller system for a wearable inflatable compression therapy garment. With reference to FIG. 5, a detachable controller 500 for a wearable inflatable compression therapy garment 110 may include a communication display device 505 communicatively coupled with pluggable controller module 510 for operative control of the compression therapy garment. In some embodiments, the pluggable controller module 510 may interchangeably interface via pluggable interface 515 with compression therapy garment 110 to operate the compression therapy garment. In various implementations, the communication display device may be a smartphone. In various implementations, the pluggable controller may be wirelessly coupled to a smartphone. In some embodiments the pluggable interface 515 may include glue logic or signal conditioning circuits to adapt the detachable controller to the electrical characteristics of various compression therapy garment electrical interfaces. In some implementations, power and ground may be provided by the smartphone. In other implementations, power and ground may be provided by a power source either integrally formed or releasably coupled to the compression therapy garment 110.

In various implementations, the pluggable interface 515 may interconnect the detachable controller to each of the sensors 225, each of the pumps 270, and each of the valves 275 for dynamic control of compression therapy in response to control input from the detachable controller or from a remote device. In some designs, a physician workstation 130 may control the compression therapy or interact with the patient from a remote location. In further designs the pluggable controller module 510 or a smartphone may download therapy protocols from the remote data warehouse 125. In further embodiments, the pluggable controller module 510 or smartphone may upload patient response (e.g., biosense) data or measurements of treatment outcomes to the remote data warehouse 125. In other designs, the pluggable controller may provide status, which may include the result of treatment, to a physician or other user via the communication display device. In other embodiments, sensors, pumps, and valves may be operably interconnected via the pluggable interface to the pluggable controller by a communication and control network 520.

In some designs, the communication and control network between the pluggable interface 515 and the peripheral devices (e.g., pumps, valves, sensors) may be arranged in, for example, a serial (e.g., two wire bus) communication bus, or a star network. In further embodiments, the communication and control network may include discrete electrical connections to all devices throughout the inflatable compression therapy garment, with all connections arriving separately from all points of the garment. In other designs, the communication and control network may be a buss connected to all devices in parallel, with a logical addressing of the target device. In some designs, the pluggable controller may include a processor, memory, a communication interface, and processor-executable program instructions directing the pluggable controller to communicate with a smartphone for operative control and monitoring of compression therapy by a smartphone application.

In some embodiments, the detachable pluggable controller 510 may be controlled by a smartphone. In other embodiments, the detachable pluggable controller 510 may be a mobile device (e.g., a smartphone), with the smartphone adapted to execute an application program (APP) and provide an interface to the compression therapy garment 110. In further embodiments, the smartphone may be adapted to plug into, or dock with, the compression therapy garment 110 directly and without a separate detachable pluggable controller 510. In such examples, the smartphone may directly control the garment, as well as provide bi-directional communication links, via a wide area network (e.g., the Internet), to third parties, such as the physician workstation 130, the remote data warehouse 125, and the device manufacturer (who may provide updates to improve performance or enable access to advanced features or therapeutic profiles, algorithms, and the calibration, for example).

As depicted, the compression therapy garment 110 includes a pocket 525 to removably retain the pluggable controller module 510. In various implementations, the compression therapy garment 110 may include multiple inflatable chambers 530. In other implementations, each inflatable chamber 530 of a compression therapy garment 110 may be individually configured with pumps, valves, or sensors independently servicing each of the inflatable chambers 530, and providing unique and independent control and monitoring of each inflatable chamber 530.

Although various embodiments have been described with reference to the Figures, other embodiments are possible. For example, some embodiments may have other sensors. For example, a temperature sensor may be included in the compression garment. The temperature sensor may be used to evaluate a person's body temperature and/or the garment temperature. If the garment temperature exceeds a predetermined threshold, the controller may evacuate the chambers and re-inflate the chambers with cooler air, for example. In some embodiments, the controller may receive a user temperature setting against which the garment temperature is compared.

In some implementations, a compression therapy garment may include one or more integral pumps to inflate one or more inflatable chambers embedded in the garment. In some examples, one or more small weep holes may vent or release pressure from an inflatable chamber, for example, to ambient atmosphere, or to another chamber. In some implementations, the pump may be controllable, alone or in combination with one or more valves, to provide an adjustable flow rate to a selected chamber.

Various embodiments may have various environmental sensors. For example, some embodiments may include an ambient temperature sensor. In an exemplary embodiment, a barometric pressure sensor may provide an ambient pressure signal to an active compression therapy system. The active compression therapy system may adjust an intensity of therapy based upon an ambient pressure, for example. In an exemplary embodiment, the inflation pressure may be increased when the ambient pressure is low, for example. Such increased pneumatic pressure may help compensate for low ambient pressures. In some embodiments the control of pneumatic pressure may assist in normalizing a treatment regime, as uncontrolled parameters affecting the treatment may vary.

In some embodiments, the controller may be affixed to the compression garment. In some embodiments, the user may be pneumatically coupled to the compression garment via one or more air conducting tubes. In some embodiments the controller may be electrically coupled to a compression garment that has one or more electrical device attached. By way of example and not limitation, a suitable pneumatic pump is commercially available from Nextern, Inc. of St. Paul, Minn.

In some embodiments more than one pump may be coupled to an active-compression therapy garment. For example, in some embodiments, each chamber may have a dedicated pump associated with that chamber. In various embodiments, each pump may be pneumatically coupled to two, three, four, five, or any reasonable number of chambers in a garment. In some embodiments, a pump pneumatically coupled to small chambers may be coupled to more chambers than a pump pneumatically coupled to larger chambers. For example, in an exemplary embodiment, a first pneumatic pump is pneumatically coupled to five chambers, and a second pneumatic pump is pneumatically coupled to three chambers whose total volume is greater than the total volume of the five chambers pneumatically coupled to the first pneumatic pump. In some embodiments, the pumps may be coupled to chambers in a way that causes the chambers to inflate in a sequenced fashion. For example, a pump may be pneumatically coupled to a first of a set of series coupled chambers. The first of the series coupled chambers may inflate before the second, and so forth. In some embodiments inflation rates may be controlled by tube diameters, for example.

In some embodiments the compression garment may be a customized compression garment designed to substantially encase a particular body part. Exemplary devices with a compression garment designed to treat a particular body part may deliver optimized therapy specific to the body part. For example, in various implementations, the compression garment may be customized to substantially encase a foot, for use in compression therapy to treat a sprained ankle. In some embodiments, the compression garment may be designed to substantially encase a lower leg, below the knee, for compression therapy to treat phlebitis. In various implementations, the compression garment may comprise a garment fitted to be worn about at least a portion of the patient's leg, the portion of a patient's leg substantially encased above or below the knee. In some embodiments, the compression garment may be designed to substantially encase a patient's knee. In various implementations, the compression garment may be designed to substantially encase a patient's elbow. In further implementations, the compression garment may be customized to substantially encase a variety of body parts, including: thigh, calf, whole leg, forearm, upper arm, whole arm, hand, wrist, elbow, shoulder, chest, torso, whole head, neck, throat, skull cap, face, or whole body. In some embodiments the compression garment may be configured in the form of: pants, a hat, a glove, a wristband, a sock or stocking, a belt, a shoe, a boot, a coat, a collar, or a cuff. In various designs a particular compression garment may be adjustable or configurable to adapt to a variety of body parts or a variety of users. Exemplary devices may be configured with adjustments such as straps, buckles, or fasteners, to adapt a compression garment to the size of a body part. In various implementations, the compression garment may be adjusted to fit an adult's larger thigh, by adapting the fit of the compression garment using the buckles, straps, or fasteners, and in a similar manner, the compression garment may be adjusted to adapt the compression garment to fit a child's forearm. In some embodiments, the compression garment may have a plurality of inflatable chambers disposed to selectively apply compression therapy to particular regions of the patient's body part. Exemplary devices may have inflatable chambers substantially disposed along one surface or region of the compression garment. For example, a compression garment designed to treat the patient's migraine headache may be configured to fit over the patient's head and provide compression to the skull, including the sides of the head and the forehead. In some embodiments, the compression garment designed to treat the patient's migraine headache may have a plurality of inflatable chambers disposed in the regions engaging the skull, including the sides of the head and the forehead. In various implementations, the compression garment may be designed with inflatable chambers disposed in the region of the patient's face, to apply compression therapy to the sinus area, but having no inflatable chambers in the rear of the skull.

Various implementations may comprise a plurality of compression garments. In some embodiments, more than one compression garment may be controlled to provide compression therapy to a patient. For example, the controller may provide compression therapy by using a leg compression garment and an arm compression garment at the same time. In some designs, the total force applied to a patient's body by multiple compression garments may be monitored and constrained to a predetermined threshold. In various embodiments, the total force applied to a patient's body may be constrained as a function of the patient's blood pressure, temperature, respiration rate, or heart rate. In some designs, inflatable chambers may be pressurized with air that is warmer or colder than ambient temperature. Exemplary devices may combine compression therapy with heat or cold therapy. For example, a compression garment designed to treat a patient's migraine headache, or a compression garment designed to treat sinus pressure, may be configured with one or more inflatable chamber and associated pneumatic engine adapted to deliver heat or cold therapy in addition to compression therapy. Exemplary devices may deliver heat or cold therapy within predetermined treatment temperature thresholds, in combination with compression therapy.

In an exemplary embodiment, a garment connected controller may be configured to operate a therapy regime autonomously from a mobile device. For example, the garment coupled controller may be in communication with the mobile device before a therapy schedule is performed. During this communication, a user may, for example, select a specific therapy schedule. The mobile device may then transmit a program that the controller will execute that effects the selected therapy schedule. The controller may then autonomously execute the received program and obtain periodic sensor data during the therapy schedule. The controller may then upload the sensor data at any convenient time. For example, the controller may upload the sensor data when the mobile device requests such data. This request may be issued during the execution of the therapy program or at a later time.

In some embodiments, a garment connected controller may be configured to operate under the direction of a mobile device. In some embodiments, the mobile device may wirelessly communicate with the controller. In some embodiments, the mobile device may communicate with the controller over a wired connection. In an exemplary embodiment, the controller may perform low level operations such as started and stopping one or more pneumatic pumps, opening and closing one or more air valves, and transmitting sensor signals to the mobile device. In some embodiments, higher level operations, such as timing events, coordinating operations, or data analysis, for example, may be performed by the mobile device. Such a low-level only capable controller may advantageously be low-cost, for example.

In some embodiments one or more types of data may be collected regarding a therapy session. For example, some embodiments may collect various forms of objective data. For example, health data and/or device data may be collected during a therapy session. By way of example and not limitation, health data may include, for example, limb density, body temperature, heart rate, blood pressure, blood flow. Blood pressure may be sensed, for example to ensure that the active compression device does not inadvertently act as a tourniquet on the limb of the patient. By way of example and not limitation, device data may include chamber pressure, garment temperature, garment movement, or garment location. For example, garment temperature may be monitored so as to ensure patient comfort. If the garment temperature becomes elevated, the pumps may replace the chambers with fresh cool air, for example. In some embodiments, data analysis may be performed on the mobile device.

Subjective data may be collected by querying the patient via a user interface, for example. In some embodiments, the controller may have a user interface for such a query. In an exemplary embodiment the user interface of the mobile device may be used to query the patient. By way of example and not limitation, questions such as: "are you comfortable?"; "is the temperature acceptable?"; or, "is the pressure not excessive?" may be asked of the patient. The patient may then respond to these and other questions. The objective and/or subjective data may then be used to dynamically adjust a therapy routine, in some embodiments. In some embodiments the objective and/or subjective data may be logged for review by the patient and/or a third party.

In some embodiments a patient may create an accessible database. For example, a database may be created online for access by the patient and/or third partied. For example, a child of an elderly patient may be granted access to the patient's database. The child may access the database so as to supervise the elderly patient's therapy, for example. A physician may be granted access to the database to monitor the health of the patient. In some embodiments the manufacturer may be granted access to the database so as to make intelligent product improvements. Health organizations may be granted access to the patient's data so as to be able to assess specific health concerns affecting the population.

Some aspects of embodiments may be implemented as a computer system. For example, various implementations may include digital and/or analog circuitry, computer hardware, other sensors (e.g. temperature sensors), firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer. For example, wearable devices, such as Google Glass or other technologies may facilitate input and/or output operations between a user and a system.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g/n, Wi-Fi, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated. In addition to the embodiments explicitly or implicitly described herein, other implementations are contemplated within the scope of the following claims.

What is claimed is:

1. An ambulatory compression therapy apparatus comprising:
    a compression garment configured to be worn by a patient while providing compression therapy to the patient, the garment comprising:
        at least one pump and one or more valves integrally coupled within the compression garment to provide inflation of one or more inflatable chambers in response to pump control signals and valve control signals; and,
        an electrical interface: (1) operably coupled to the at least one pump and the one or more valves and (2) integrated within the compression garment, and
    a compression garment controller, affixed to the compression garment, configured to operatively connect directly to the electrical interface and generate the pump control signals to send to the at least one pump, and the valve control signals to send to the one or more valves, to control inflation of each of the one or more inflatable chambers according to a predetermined compression therapy profile via the electrical interface, wherein the compression garment controller is non-pneumatically coupled to the at least one pump and one or more valves; and a portable energy storage device attachable to the compression garment to supply operating power to perform the predetermined compression therapy, wherein the garment is configured to deliver to the patient the compression therapy according to a predetermined compression therapy profile while the patient is ambulatory and physically untethered to any other devices.

2. The apparatus of claim 1, wherein the compression garment controller comprises a mobile telecommunications device that is physically unconnected to the compression garment when the compression garment is released from the electrical interface.

3. The apparatus of claim 2, wherein the compression garment controller is in wireless communication with the mobile telecommunications device.

4. The apparatus of claim 2, wherein the mobile telecommunications device is in data communication with the compression garment and operable to establish a communication link with a remote server to receive from the remote server information to define the predetermined compression therapy profile, and to communicate the received information to the compression garment controller.

5. The apparatus of claim 1, wherein the electrical interface is pluggable and configured to releasably attach to the compression garment controller.

6. The apparatus of claim 1, wherein the compression garment controller is integrated into the compression garment.

7. The apparatus of claim 1, wherein the compression garment comprises a garment fitted to be worn about at least a portion of a foot of the patient.

8. The apparatus of claim 1, wherein the compression garment comprises a garment fitted to be worn about at least a portion of a leg of the patient.

9. The apparatus of claim 1, wherein the compression garment comprises a garment fitted to be worn about at least a portion of an arm of the patient.

10. The apparatus of claim 1, wherein the compression garment comprises a garment fitted to be worn about at least a portion of a neck of the patient.

11. The apparatus of claim 1, wherein the compression garment comprises a garment fitted to be worn about at least a portion of a head of the patient.

12. The apparatus of claim 1, wherein the compression garment comprises a garment fitted to be worn about at least a portion of a torso of the patient.

13. The apparatus of claim 1, wherein the compression garment further comprises a pocket for storing the compression garment controller.

14. The apparatus of claim 1, wherein the compression garment controller comprises:

a processor; and, a program memory tangibly embodied in a machine-readable storage device, the program memory storing instructions that, when executed by the processor, cause the processor to perform operations to adjust the predetermined compression therapy profile as a function of a disease state of the patient by executing at least one artificial-intelligence technique for adaptive treatment adjustment.

15. A wearable compression therapy apparatus, comprising:

a compression garment configured to be worn by a patient while providing compression therapy to the patient, the garment comprising:

at least one pump and one or more valves operatively coupled and integrated within the compression garment to provide inflation of one or more inflatable chambers in response to pump control signals and valve control signals; and, an electrical interface: (1) operably coupled to the at least one pump and the one or more valves, and (2) integrally attached to the compression garment; and, a compression garment controller, affixed to the compression garment, the compression garment controller configured to operatively connect directly to the electrical interface, and configured to generate the pump control signals to send to the at least one pump, and the valve control signals to send to the one or more valves, to control inflation of each of the one or more inflatable chambers according to a predetermined compression therapy profile via the electrical interface, wherein the compression garment controller is non-pneumatically coupled to the at least one pump and one or more valves, wherein the garment is configured to deliver to the patient the compression therapy according to the predetermined compression therapy profile while the patient is ambulatory and physically untethered to any other devices.

16. The apparatus of claim 15, wherein the compression garment controller is integrated into the compression garment.

17. The apparatus of claim 15, wherein the mobile telecommunications device is in data communication with the compression garment controller and operable to establish a communication link with a remote server to receive, from the remote server, information to define the predetermined compression therapy profile, and to communicate the received information to the compression garment controller that is configured to generate the pump control signals to send to the at least one pump, and the valve control signals to send to the one or more valves, to control inflation of each of the one or more inflatable chambers according to the predetermined compression therapy profile.

18. The apparatus of claim 15, wherein the compression garment controller is in wireless communication with a mobile telecommunications device.

19. The apparatus of claim 15, wherein the electrical interface is pluggable and configured to releasably attach to the compression garment controller.

20. A wearable compression therapy apparatus comprising:

a compression garment configured to be worn by a patient while providing compression therapy to the patient, the garment comprising:

at least one pump and one or more valves integrally coupled within the compression garment to provide inflation and deflation of one or more inflatable chambers in response to pump control signals and valve control signals;

an electrical interface: (1) operably coupled to the at least one pump and the one or more valves, and (2) integrally attached within the compression garment; and, means for receiving from a remote server information to define a predetermined compression therapy profile; and, means for generating the pump control signals to send to the at least one pump, and the valve control signals to send to the one or more valves, to control inflation and deflation of each of the one or more inflatable chambers according to the predetermined compression therapy profile via the electrical interface, wherein the means for generating the pump control signals is affixed to the compression garment and configured to operatively connect directly to the electrical interface, and, wherein the means for generating the pump control signals is non-pneumatically coupled to the at least one pump and one or more valves.

\* \* \* \* \*